United States Patent [19]

Nakamura et al.

[11] Patent Number: 5,637,585
[45] Date of Patent: Jun. 10, 1997

[54] CRYSTAL FORM OF BENZODIAZEPINE DERIVATIVES

[75] Inventors: Makoto Nakamura, Ibaraki; Kouichi Watanabe, Fukushima, both of Japan

[73] Assignee: Yamanouchi Pharmaceutical Co., Ltd., Tokyo, Japan

[21] Appl. No.: 578,573

[22] PCT Filed: Jul. 5, 1994

[86] PCT No.: PCT/JP94/01094

§ 371 Date: Dec. 21, 1995

§ 102(e) Date: Dec. 21, 1995

[87] PCT Pub. No.: WO95/01964

PCT Pub. Date: Jan. 19, 1995

[30] Foreign Application Priority Data

Jul. 6, 1993 [JP] Japan ........................... 5/191894

[51] Int. Cl.$^6$ ................ A61K 31/55; C07D 243/24

[52] U.S. Cl. .................................. 514/221; 540/509
[58] Field of Search ........................ 540/509; 514/221

[56] References Cited

FOREIGN PATENT DOCUMENTS 591529 4/1994 European Pat. Off. ........... 540/509

*Primary Examiner*—Robert T. Bond
*Attorney, Agent, or Firm*—Burgess, Ryan & Wayne

[57] ABSTRACT

This invention provides the form B crystal of (R)-1-[2,3-dihydro-1-(2'-methylphenacyl)-2-oxo-5-phenyl-1H-1,4-benzodiazepin-3-yl]-3-(3-tolyl)urea which is produced by recrystallizing the compound from a mixed solvent of at least 1 volume of water and 5 volumes of an alcohol. The form B crystals have excellent filtration property and flowability, so that they can be handled markedly easily at the time of filtration for their large scale production or when they are made into pharmaceutical preparations and therefore are useful in view of their industrial production.

10 Claims, 5 Drawing Sheets

CRYSTAL FORM OF BENZODIAZEPINE DERIVATIVES

This application is a 371 of PCT/JP 94/01094, filed Jul. 5, 1993 which claims the priority of Japanese Application 5/191,894, filed 5 Jul. 1993.

TECHNICAL FIELD

This invention relates to a novel form B crystal of (R)-1-[2,3-dihydro-1-(2'-methylphenacyl)-2-oxo-5-phenyl-1H-1,4-benzodiazepin-3-yl]-3-(3-tolyl)urea (to be referred to as "compound I" hereinafter).

BACKGROUND ART

The compound I represented by the following formula of chemical structure has been reported as a compound which has low affinity for benzodiazepine receptors, shows no significant actions on the central nervous system based on benzodiazepine receptors, but has strong CCK (cholecystokinin)-B receptor antagonism and/or gastrin receptor antagonism. This compound is useful for the treatment of digestive organ diseases such as gastric ulcer, duodenal ulcer, gastritis, reflux esophagitis, Zollinger-Ellison syndrome, gastrin-sensitive pancreatitis and the like and central nervous system-related diseases such as appetite controlling system disorders, pain, anxiety and the like (cf. International Publication WO 92/11246).

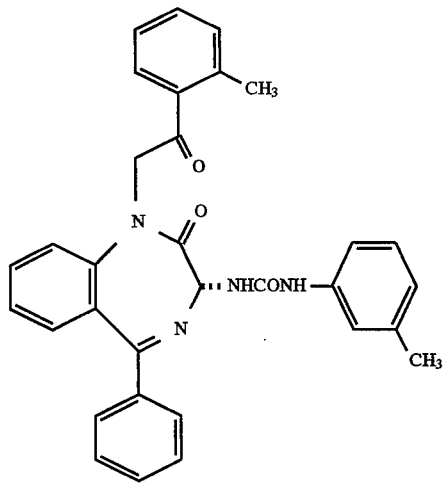

(I)

According to Example 16 of the above patent publication, crystals of compound I (to be referred to as "crystal form A" hereinafter) are obtained when compound I is crystallized from a toluene-n-hexane mixed solution or a methylene chloride-ether mixed solution. The A form crystals have following physicochemical properties.

$[\alpha]^{20}_D = +138.1°$ (c=0.99, $CH_2Cl_2$)

Melting point: 197° to 199° C.

Elemental analysis data (for $C_{32}H_{28}N_4O_3$)

|  | C (%) | H (%) | N (%) |
|---|---|---|---|
| calcd. | 74.40 | 5.46 | 10.85 |
| found | 74.45 | 5.53 | 10.88 |

Mass spectrometry data FAB, Pos. (m/z): 517 ($M^+ + 1$)

DISCLOSURE OF THE INVENTION

The object of the present invention is to provide the aforementioned B form crystals, as well as a process for the production of B form crystals, B form crystals obtained by said process and a pharmaceutical composition which contains B form crystals.

The inventors of the present invention have conducted extensive studies on other crystal forms of the compound I and found the novel crystal form B which can be handled markedly easily at the time of filtration for the large scale production or when they are made into pharmaceutical preparations, hence resulting in the accomplishment of the present invention. As shown in Table 1, the B form crystals of compound I according to the present invention are novel crystals whose physicochemical properties are clearly different from those of the known A form crystals.

In this connection, DSC (differential scanning calorimetry) patterns of the B form crystals of the present invention and the A form crystals are shown in FIGS. 1 and 2, their powder X-ray diffraction patterns in FIGS. 3 and 4, and their particle size distribution patterns in FIGS. 5 and 6.

TABLE 1

|  | Inventive B form crystal | Form A crystal |
|---|---|---|
| Melting point | 187 to 190° C. | 197 to 199° C. |
| DSC | Endothermic peak at around 191° C. | Endothermic peak at around 196° C. |

| Powder X-ray diffrac- tion | Lattice plane spacing (Å) | Relataive intensity of diffraction | Lattice plane spacing (Å) | Relative intensity of diffraction |
|---|---|---|---|---|
|  | 12.6 | 100 | 12.3 | 100 |
|  | 11.5 | 44 | 10.6 | 70 |
|  | 5.7 | 32 | 5.7 | 64 |
|  | 5.9 | 16 | 5.1 | 79 |
|  | 4.4 | 27 | 4.8 | 81 |
|  | 3.9 | 19 | 4.2 | 72 |
|  | 3.7 | 15 | 3.7 | 54 |
| Form | Crystalline powder or crystals |  | Crystalline powder |  |

As is evident from Table 1, DSC patterns, powder X-ray diffraction patterns and forms, the B form crystals of the present invention are novel crystals whose melting point, DSC, X-ray diffraction, form, etc. are completely different from those of the A form crystals.

(Production Method)

While A form crystals are produced by recrystallizing compound I from an organic solvent such as a toluene-n-hexane mixed solution, a methylene chloride-ether mixed solution, ethanol or the like, the B form crystals of the present invention are obtained by recrystallizing the compound from a water-containing solvent, illustratively by recrystallizing compound I from an aqueous alcohol composed of 1 to 10 volumes of water and 5 volumes of an alcohol (e.g., ethanol), preferably about 1.5 to 1.7 volumes of water and 5 volumes of alcohol.

Since the B form crystals of the present invention tend to be obtained easily as the ratio of water increases, the volumetric ratio of water to alcohol for the recrystallization of the B form crystals is not limited to 10 or less water to 5 alcohol. When the ratio of water is 10 or more, however, a large volume of recrystallization solvent (total volume) is required in view of the solubility of the B form crystals.

The B form crystals of the present invention are made into tablets, powders, fine granules, capsules, pills, solutions, injections, suppositories, ointments, plasters and the like and administered orally (including sublingual administration) or parenterally.

Solid or liquid non-toxic pharmaceutical materials may be used as pharmaceutically acceptable carriers and excipients for the production of pharmaceutical preparations. Illustrative examples of such materials include lactose, magnesium stearate, starch, talc, gelatin, agar, pectin, gum arabic, olive oil, sesame oil, cacao butter, ethylene glycol and other conventionally used materials.

Clinical dose of the crystals of the present invention is optionally decided taking into consideration symptoms, body weight, age, sex and the like of each patient to which the crystals are administered, but it may be generally within the range of from 1 to 1,000 mg per day per adult in the case of oral administration, and the daily dose recited above may be divided into several doses per day.

INDUSTRIAL APPLICABILITY

Figure 1:
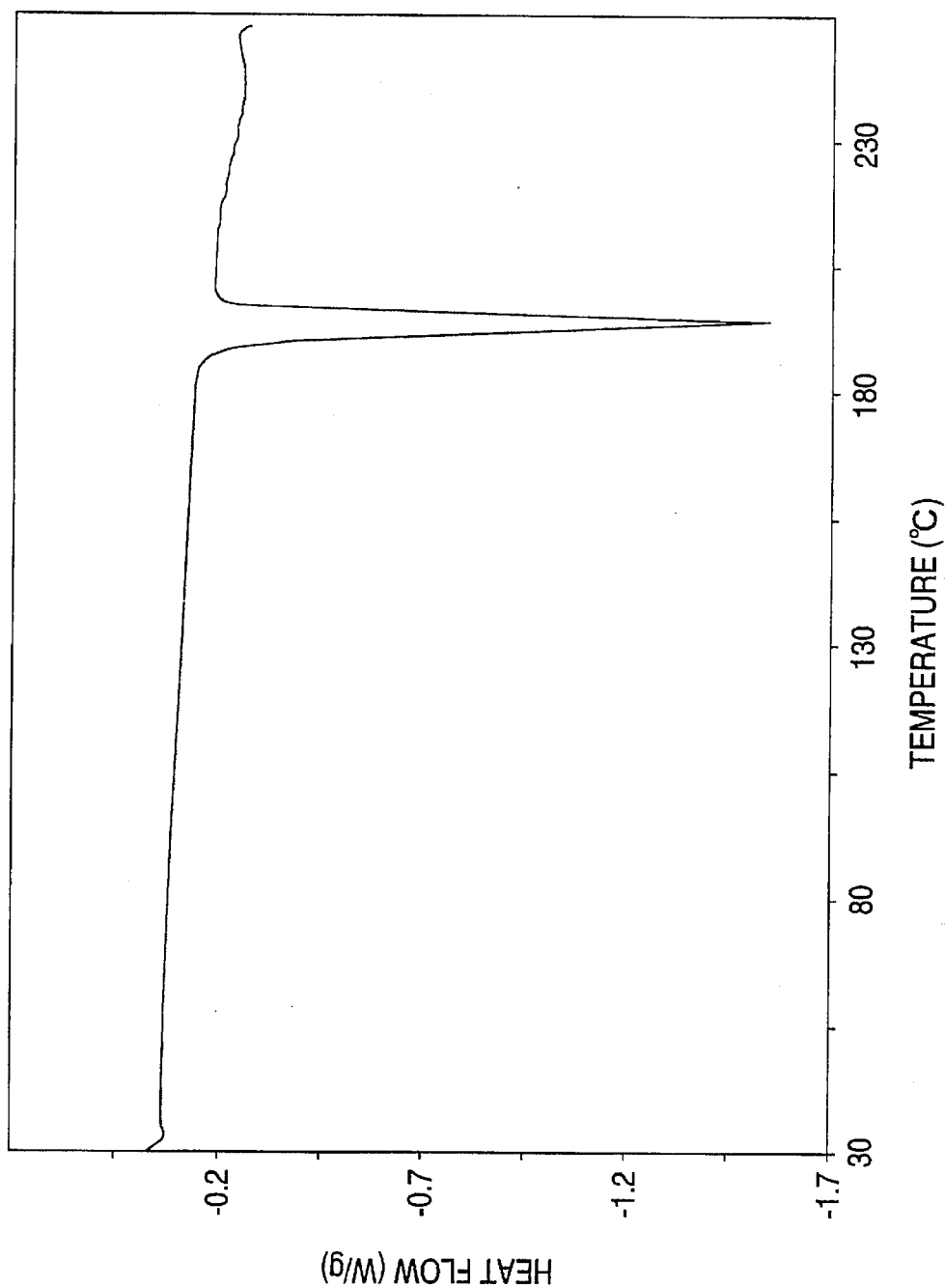
FIG. 1 is a DSC pattern of B form crystals of the present invention.
Figure 2:
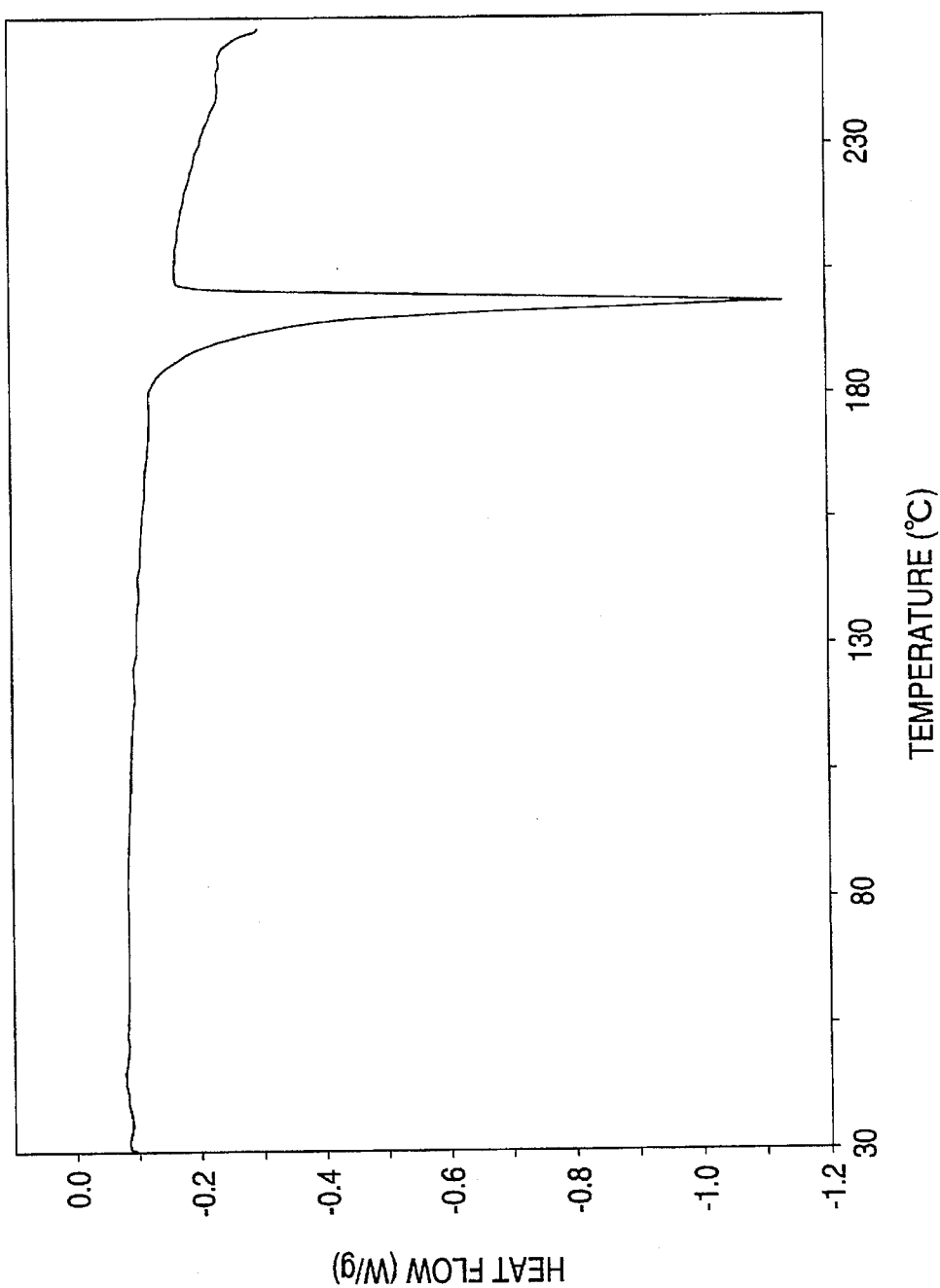
FIG. 2 is a DSC pattern of the A form crystals.

The B form crystals of the present invention have excellent filtration property and flowability, are almost free from scattering since they have a large particle size, and have low charging property and the like. Accordingly, they have an advantage in that they can be handled markedly easily at the time of filtration for the large scale production or when they are made into pharmaceutical preparations.

In consequence, the B form crystals are markedly useful when the compound I is produced in an industrial scale and made into pharmaceutical preparations.

In addition, the B form crystals of the present invention do not show hygroscopicity and are stable at least for 3 months against temperature (room temperature to 80° C.), moisture (75% relative humidity at 40° C.) and light (indoor light).

In order to compare B form crystals of the present invention with A form crystals, (1) filtration property test, (2) particle size distribution (average particle size and 50% cumulative particle size) measuring test, (3) sedimentation specific volume measuring test and (4) charging property test were carried out as in the following.

(1) Filtration property test

The filtration property test to compare B form crystals of the present invention with A form crystals was carried out in the following manner using the same glass filter.

A Form crystals: After dissolving 60 g of compound I in 720 ml of ethanol with heating, A form crystals were seeded at about 50° C. The solution was gradually cooled and stirred overnight at 35° C. and then for 5 hours at 0° C., and the thus precipitated crystals were subjected to suction filtration using a G-3 glass filter of 16.5 cm in diameter (filtration area, 214 cm$^2$). At that time, the time required for the suction filtration was measured as a filtration time (sec). The filtration time was defined as a period from the commencement of filtration until outflow of the filtrate became 1 drop or less per 1 second. The thus collected crystals were dried for 3 days at room temperature to obtain 50.06 g of A form crystals. They were confirmed to be A form crystals by DSC and powder X-ray diffraction. Also, a filtration rate (amount of filtered crystals (g)/filtration area (cm$^2$)·filtration time (sec)) was obtained by calculation.

B Form crystals of the present invention: After dissolving 60 g of compound I in 1,800 ml of ethanol with heating, 540 ml of hot water of about 50° C. was added thereto and B form crystals were seeded therein when the temperature of the solution reached 50° C. The solution was gradually cooled and stirred overnight at 35° C. and then for 5 hours at 0° C., and the thus precipitated crystals were subjected to suction filtration using a G-3 glass filter of 16.5 cm in diameter (filtration area, 214 cm$^2$). At that time, the time required for the suction filtration was measured as a filtration time (sec). The filtration time was defined as a period from the commencement of filtration until outflow of the filtrate became 1 drop or less per 1 second. The thus collected crystals were dried for 3 days at room temperature to obtain 50.96 g of B form crystals of the present invention. They were confirmed to be B form crystals by DSC and powder X-ray diffraction. Also, a filtration rate (amount of filtered crystals (g)/filtration area (cm$^2$)·filtration time (sec)) was obtained by calculation.

Results of the test are shown in Table 2

TABLE 2

| Crystal form | Inventive B form crystal | A form crystal |
| --- | --- | --- |
| Amount of filtered crystals (g) | 50.96 | 50.06 |
| Filtration area (cm$^2$) | 214 | 214 |
| Filtration time (sec) | 190 | 760 |
| Filtration rate (g/cm$^2$ sec) | 12.53 × 10$^{-4}$ | 3.08 × 10$^{-4}$ |

It is evident that B form crystals of the present invention are markedly excellent in their filtration property, because their filtration rate is about 4 times larger than that of A form crystals. This is considerably advantageous in terms of the improvement of workability and shortening of working time when the compound is produced industrially in a large scale.

Figure 5:
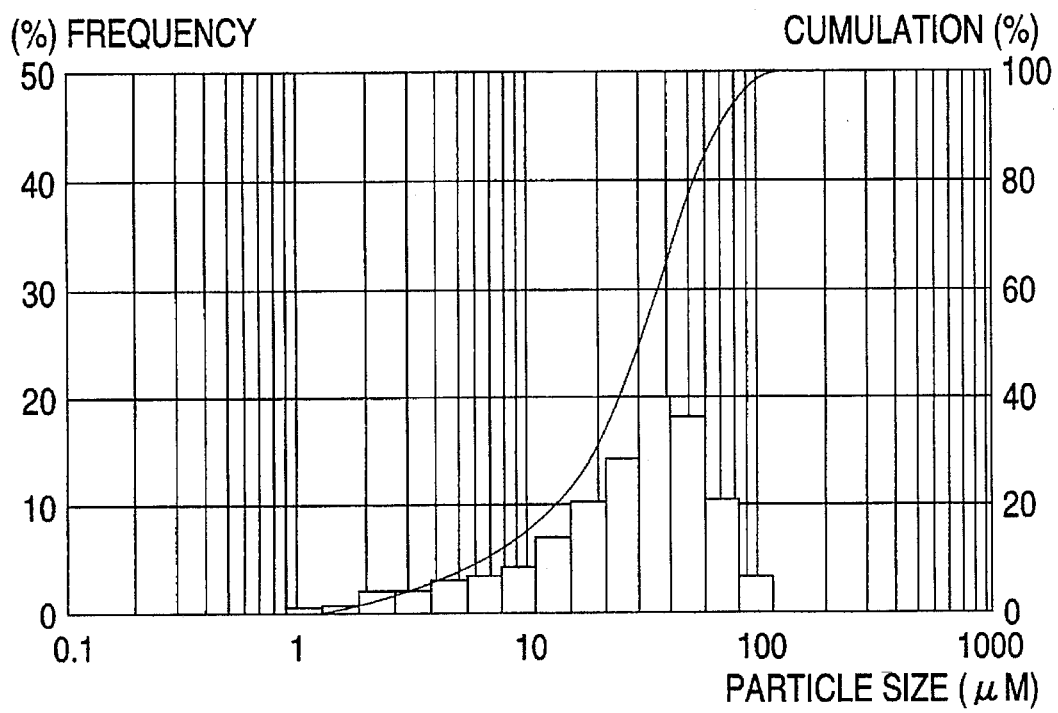
FIG. 5 is a particle size distribution pattern of B form crystals of the present invention.
Figure 6:
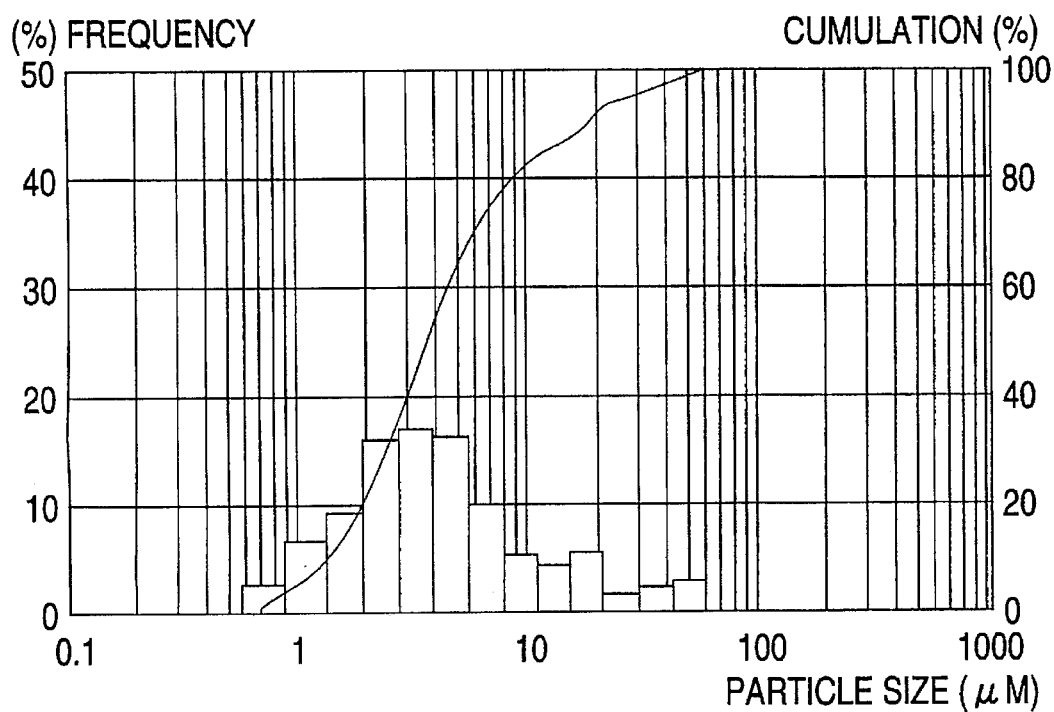
FIG. 6 is a particle size distribution pattern of A form crystals.

(2) Particle size distribution (average particle size and 50% cumulative particle size) measuring test Particle sizes of B form crystals of the present invention and A form crystals were measured by the laser diffraction method, with the results shown in FIG. 5 (inventive B form crystals) and FIG. 6 (A form crystals).

Also, measured data of average particle sizes and 50% cumulative particle sizes are shown in Table 3.

TABLE 3

| Crystal form | Inventive B form crystal | A form crystal |
| --- | --- | --- |
| Average particle size (μm) | 35.45 | 7.35 |
| 50% Cumulative particle size (μm) | 32.29 | 3.74 |

Measuring apparatus:
  Microtrack MKII SPA, manufactured by Nikkiso
  (measuring principle: laser diffraction;
  measuring range: 0.7 to 700 μm)
Measuring conditions:
  amount of sample: about 50 mg;
  solvent: about 200 ml of n-hexane;
  dispersion: 120 sec in ultrasonic oscillator The B form crystals of the present invention can be regarded as crystals which are hardly scattered, because they are about 4.8 times larger in average particle size and about 8.6 times larger in 50% cumulative particle size in comparison with A form crystals. This is advantageous in terms of the workability and working environment when handled industrially in a large quantity.

In this connection, the term "average particle size" means an average particle size of volume load, and the term 50% cumulative particle size means a particle size corresponding to 50% of cumulative distribution (Funtaikogakuyogojiten (Dictionary of Powder Technology), edited by Society of Powder Technology, first edition and first printing published by Nikkan Kogyo Shinbun-sha on Dec. 15, 1981).

(3) Sedimentation specific volume measuring test

The B form or A form crystals (each 1 g) were suspended (by shaking 20 times) in 20 ml of ethanol (21° C.) contained in a measuring cylinder and allowed to precipitate for 1 hour to measure their volume.

The measurement was repeated 3 times to obtain the average value, with the results shown in Table 4.

TABLE 4

| Crystal form | Inventive B form crystal | A form crystal |
| --- | --- | --- |
| Sedimentation specific volume (ml/g) | | |
| 1 | 3.3 | 15.7 |
| 2 | 3.3 | 16.7 |
| 3 | 3.6 | 15.5 |
| Average | 3.4 | 16.0 |

Sedimentation specific volume of B form crystals of the present invention is about ⅕ of that of A form crystals. It can be said in general that smaller sedimentation specific volume means smaller interaction between particles and superior flowability (Funtaikogakuyogojiten cited above), so that it can be said that the B form crystals of the present invention are excellent in flowability in comparison with the A form crystals. In consequence, the B form crystals of the present invention are markedly easy to handle in the steps of drying, transferring, making pharmaceutical preparations and the like when the compound is produced industrially in a large scale.

(4) Charging property test

About 47 to 50 g of the B form or A form crystals were put into a polyethylene bag of 17 cm in width, 15 cm in depth and 40 cm in height, shaken for 1 minute to generate static electricity and then poured into a dish to measure their electric potential with a static electricity checker.

Measuring apparatus:

ES. Checker manufactured by Nippon Kayaku (measuring range: 0 to 10 KV; measuring space: 50 mm)

Since crystals partially adhere to and remain in the polyethylene bag due to static electricity when the bag is turned upside down to pour out the crystals, their recovery ratio was calculated and used as one index of the charging property. The results obtained are shown in Table 5.

TABLE 5

| Crystal form | Inventive B form crystal | A form crystal |
| --- | --- | --- |
| Charge voltage (KV) | 0 | 3 |
| Recovery ratio (%) | 98.9 (49.06 g/49.60 g) | 96.4 (45.42 g/47.12 g) |

Humidity: 46%; temperature: 23° C.

Since B form crystals of the present invention have a charge voltage of 0 KV, while A form crystals have a charge voltage of 3 KV, under above conditions, the B form crystals of the present invention have a hardly chargeable property in comparison with A form crystals.

In relative comparison of A form crystals and B form crystals of the present invention, it can be assumed that the B form crystals of the present invention have smaller potential energy to cause ignition of combustible materials (e.g., organic solvents) by discharge. In consequence, it is expected that the B form crystals have smaller possibility to cause electrostatic fire due to discharge of static electricity and therefore are safe.

In addition, since the recovery ratio of A form crystals is 96.4% and that of the B form crystals of the present invention is 98.9%, it is evident that the B form crystals of the present invention show much smaller adhesion caused by static electricity and the like.

In the practical industrial handling, crystals of the compound I collected by filtration are dried, packed in polyethylene bags and the like for shipping and then unpacked and made into pharmaceutical preparations at factories, so that the B form crystals of the present invention, in comparison with A form crystals, are crystals which cause less adhesion loss and can be handled safely and markedly easily in handling of the crystals such as packing, shipping, unpacking or the like.

As has been described in the foregoing, the B form crystals of the present invention, in comparison with the A form crystals, possess characteristics that they are excellent in filtration property, hardly scatters due to their large particle size, are excellent in flowability, and are hardly chargeable. In consequence, the B form crystals of the present invention have a great advantage in that workability and working environment can be improved when they are produced in an industrial scale, because safe and markedly easy handling can be made during the steps of filtration, drying, shipping, drug preparation and the like.

BEST MODE OF CARRYING OUT THE INVENTION

Next, the B form crystals of the present invention and production process thereof are described further in detail with reference to the following examples. In this connection, the raw material to be used in the present invention and its production method are as described in International Publication WO 92/11246.

EXAMPLE 1

(R)-3-Amino-1,3-dihydro-1-(2'-methylphenacyl)-5-phenyl-2H-1,4-benzodiazepin-2-one•(S)-mandelate (41.8 kg) was suspended in 760 l of dichloromethane and dissolved therein by adding 462 l of 0.21N sodium hydroxide aqueous solution and stirring for 30 minutes. The organic layer was washed twice with 767 l of water and the solvent was evaporated. The thus obtained free amine was dissolved in 350 l of dichloromethane, and 11.25 kg of 3-tolyl isocyanate was added to the solution, followed by stirring for 1.5 hours at room temperature to effect the reaction. The solvent in the reaction solution was evaporated, the resulting residue was dissolved in 1,087 l of ethanol with heating and then 326 l of 50° C. hot water was added to the thus prepared solution, when its temperature reached 50° C., followed by the seeding of B form crystals.

The solution was gradually cooled and stirred overnight at 35° C. and then overnight at 0° C., and the thus precipitated crystals were collected by filtration and washed with a mixed solution of 92 l ethanol and 28 l water. By drying the thus collected crystals at 40° C. for 3 days, 36.9 kg of B form crystals of (R)-1-[2,3-dihydro-1-(2'-methylphenacyl)-2-oxo-5-phenyl-1H-1,4-benzodiazepin-3-yl]-3-(3-tolyl)urea was obtained (Lot No.1).

Melting point: 189° C.

Measuring apparatus: Riken type melting point measuring apparatus PA-20S

Measuring method: According to Pharmacopoeia of Japan, 12th revision, Melting Point Measuring Method (First Method)

DSC (FIG. 1): endothermic peak at around 191° C.

Figure 3:
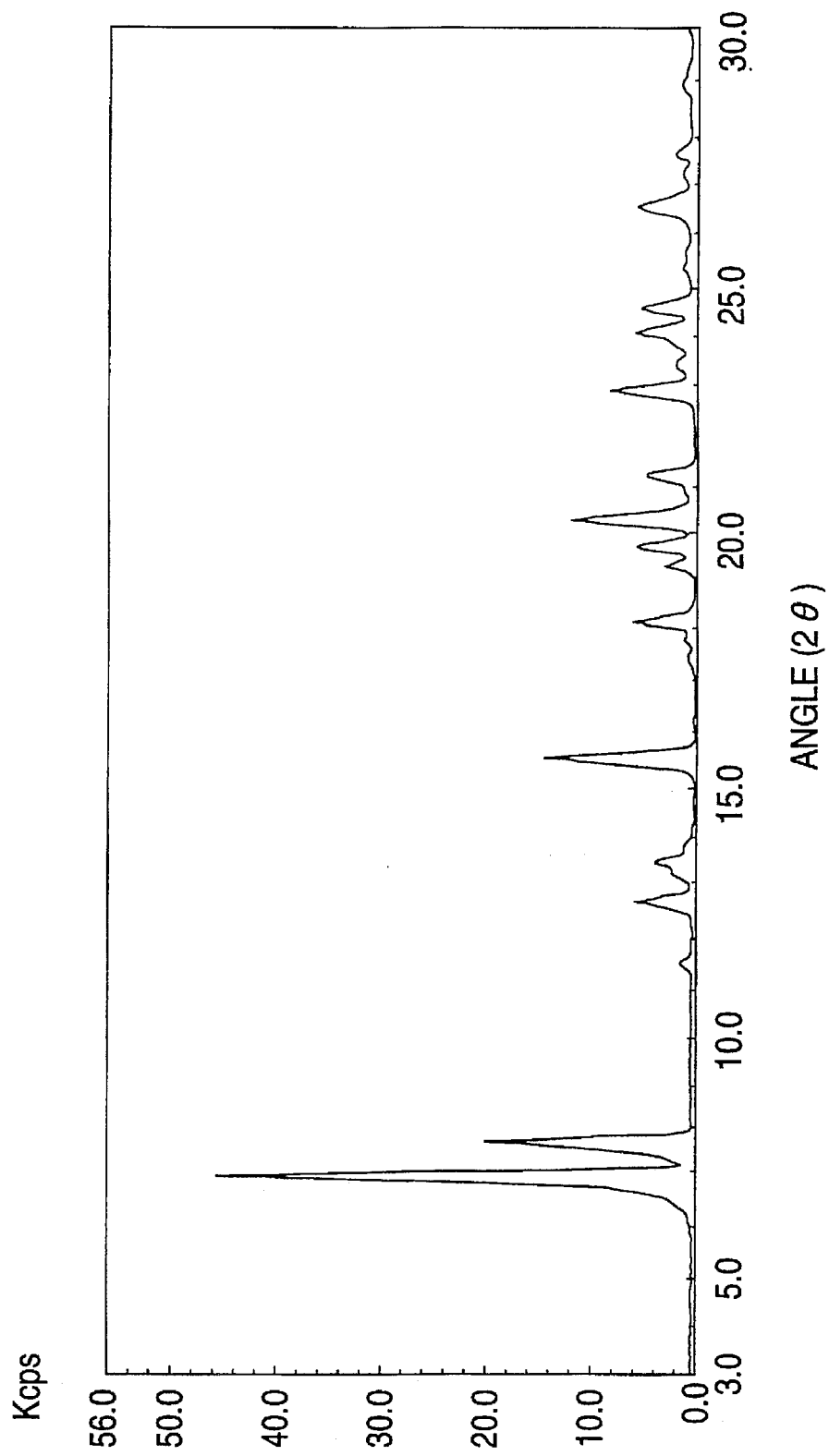
FIG. 3 is a powder X-ray diffraction pattern of B form crystals of the present invention.
Figure 4:
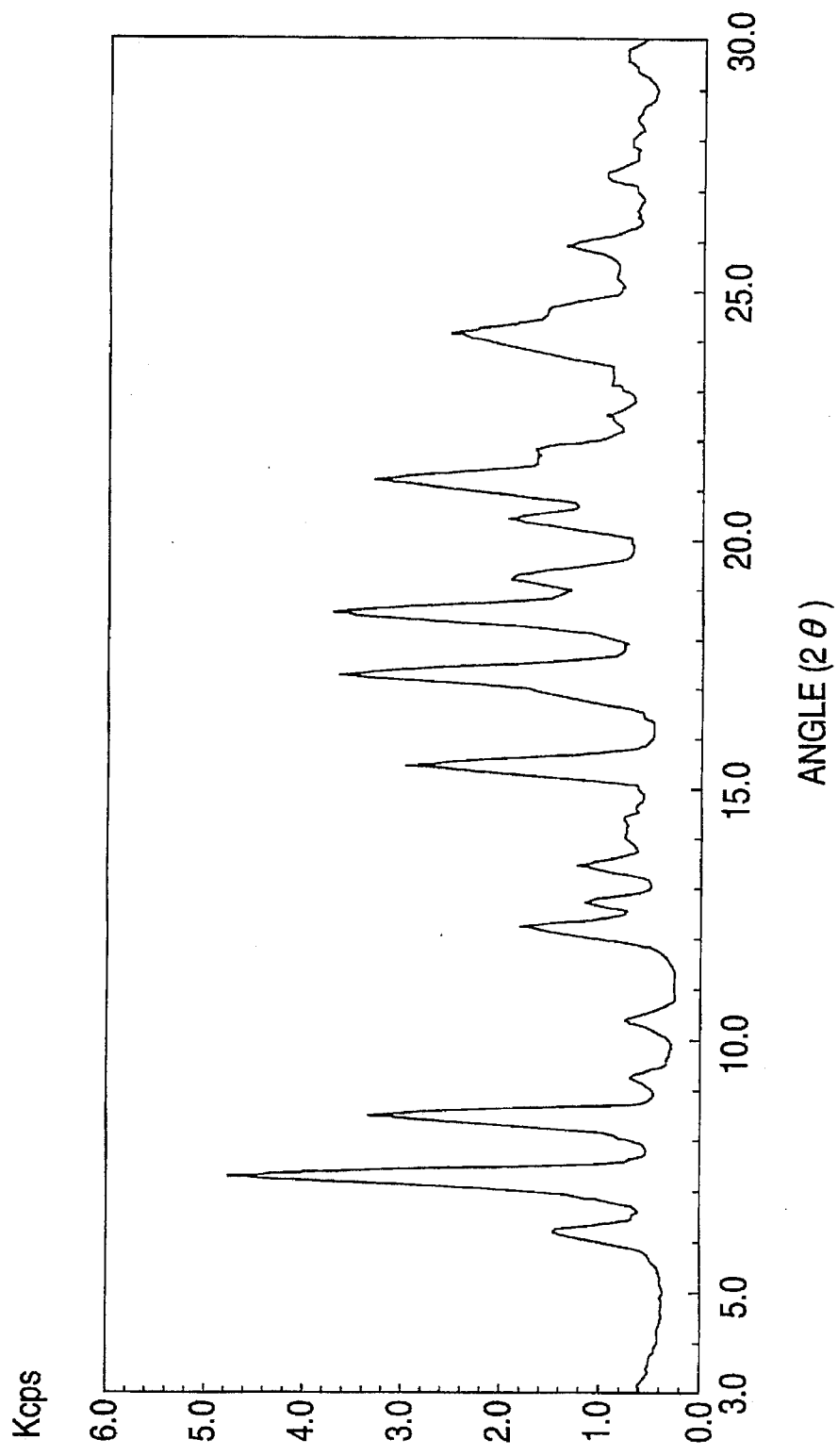
FIG. 4 is a powder X-ray diffraction pattern of A form crystals.

Measuring apparatus: Type 2200 differential scanning calorimeter manufactured by TA Instrument Measuring method: temperature rising from 30° C. to 250° C. at a rate of 5° C. per minute Powder X-ray diffraction (Table 6 and FIG. 3): Characteristic peaks are shown as relationship between lattice plane spacing and diffraction intensity.

TABLE 6

| Lattice plane spacing (Å) | 12.6 | 11.5 | 5.7 | 4.9 | 4.4 | 3.9 | 3.7 |
|---|---|---|---|---|---|---|---|
| Realtive diffraction intensity | 100 | 44 | 32 | 16 | 27 | 19 | 15 |

Measuring apparatus:
RINT-1400 manufactured by Rigaku-sha
Measuring method:
vessel: copper (40 KV, 40 mA); scan speed: 3.0°/min
Elemental analysis data (for $C_{32}H_{29}N_4O_3$)

|  | C (%) | H (%) | N (%) |
|---|---|---|---|
| calcd. | 74.40 | 5.46 | 10.85 |
| found | 74.57 | 5.49 | 10.86 |

EXAMPLE 2

Except for the use of 1,240 l of ethanol and 373 l of hot water, the process of Example 1 was repeated to obtain 40.95 kg of B form crystals of (R)-1-[2,3-dihydro-1-(2'-methylphenacyl)-2-oxo-5-phenyl-1H-1,4-benzodiazepin-3-yl]-3-(3-tolyl)urea (Lot No.2) from 47.8 kg of (R)-3-amino-1,3-dihydro-1-(2'-methylphenacyl)-5-phenyl-2H-1,4-benzodiazepin-2-one•(S)-mandelate.

Melting point: 187.8° C.

EXAMPLE 3

Except for the use of 760 l of ethanol and 152 l of hot water, the process of Example 1 was repeated to obtain 34.32 kg of B form crystals of (R)-1-[2,3-dihydro-1-(2'-methylphenacyl)-2-oxo-5-phenyl-1H-1,4-benzodiazepin-3-yl]-3-(3-tolyl)urea (Lot No.3) from 42.5 kg of (R)-3-amino-1,3-dihydro-1-(2'-methylphenacyl)-5-phenyl-2H-1,4-benzodiazepin-2-one•(S)-mandelate.

Melting point: 188.4° C.

Next, a formulation example of pharmaceutical preparation using the B form crystals of the present invention is described.

Formulation Example (tablets)

| Composition | 20 mg tablet | 40 mg tablet |
|---|---|---|
| Compound of Example 1 | 20 mg | 40 mg |
| Lactose | 73.4 | 80 |
| Corn starch | 18 | 20 |
| Hydroxypropylcellulose | 4 | 5 |
| Carboxymethylcellulose calcium | 4 | 4.2 |
| Magnesium stearate | 0.6 | 0.8 |
| Total | 120 mg | 150 mg |

Preparation of 20 mg tablets

The compound of Example 1 (100 g) was uniformly mixed with 367 g of lactose and 90 g of corn starch using a fluidized granulation coating machine (manufactured by Ohgawara Seisakusyo). To this was sprayed 200 g of 10% hydroxypropylcellulose solution to effect granulation. After drying, the resulting granules were passed through a 20 mesh screen, mixed with 20 g of carboxymethylcellulose calcium and 3 g of magnesium stearate and then applied to a rotary tablet-making machine (manufactured by Hata Tekkosyo) to produce tablets, each weighing 120 mg, making use of a die/punch system of 7 mm×8.4 R.

Preparation of 40 mg tablets

The compound of Example 1 (140 g) was uniformly mixed with 280 g of lactose and 70 g of corn starch using a fluidized granulation coating machine (manufactured by Ohgawara Seisakusyo). To this was sprayed 175 g of 10% hydroxypropylcellulose solution to effect granulation. After drying, the resulting granules were passed through a 20 mesh screen, mixed with 14.7 g of carboxymethylcellulose calcium and 2.8 g of magnesium stearate and then applied to a rotary tablet-making machine (manufactured by Hata Tekkosyo) to produce tablets, each weighing 150 mg, making use of a die/punch system of 7.5 mm×9 R.

We claim:

1. The form B crystal of (R)-1-[2,3-dihydro-1-(2'-methylphenacyl)-2-oxo-5-phenyl-1H-1,4-benzodiazepin-3-yl]-3-(3-tolyl)urea, which has the following physicochemical properties melting point: 187° to 190° C., DSC: endothermic peak at around 191° C., and powder X-ray diffraction: the following table:

| Lattice plane spacing (Å) | 12.6 | 11.5 | 5.7 | 4.9 | 4.4 | 3.9 | 3.7 |
|---|---|---|---|---|---|---|---|
| Relative diffraction intensity. | 100 | 44 | 32 | 16 | 27 | 19 | 15 |

2. A process for producing B form crystal of claim 1, which comprises recrystallizing (R)-1-[2,3-dihydro-1-(2'-methylphenacyl)-2-oxo-5-phenyl-1H-1,4-benzodiazepin-3-yl]-3-(3-tolyl)urea from a mixed solvent of at least one volume of water and 5 volumes of an alcohol.

3. The form B crystal of (R)-1-[2,3-dihydro-1-(2'-methylphenacyl)-2-oxo-5-phenyl-1H-1,4-benzodiazepin-3-yl]-3-(3-tolyl)urea, which is produced by the process of claim 2.

4. A pharmaceutical composition which comprises the B form crystal of claim 1 and a pharmaceutically acceptable carrier.

5. The process of claim 2 wherein the mixed solvent contains about 1.5 to 1.7 volumes of water and 5 volumes of an alcohol.

6. The process of claim 2 wherein the alcohol is ethanol.

7. The process of claim 5 wherein the alcohol is ethanol.

8. The pharmaceutical composition of claim 4 in the form of a clinical dose containing from 1 to 1000 mg per day per adult of the B form crystal.

9. The pharmaceutical composition of claim 4 wherein the pharmaceutically acceptable carrier is a mixture of lactose and corn starch.

10. The pharmaceutical composition of claim 8 which is in the form of a tablet.

* * * * *